United States Patent [19]

Kai et al.

[11] Patent Number: 4,889,711
[45] Date of Patent: Dec. 26, 1989

[54] COMPOSITION FOR ANTIPERSPIRANT AEROSOL

[75] Inventors: Masanobu Kai; Etsuko Chiku, both of Tokyo, Japan

[73] Assignee: Kao Corporation, Tokyo, Japan

[21] Appl. No.: 229,757

[22] Filed: Aug. 8, 1988

Related U.S. Application Data

[63] Continuation of Ser. No. 943,704, Dec. 19, 1986, abandoned.

[30] Foreign Application Priority Data

Jan. 14, 1986 [JP] Japan ................................ 5746/1986

[51] Int. Cl.$^4$ .................... A61K 7/34; A61K 7/38; A61K 9/12
[52] U.S. Cl. .................................. 424/47; 424/66; 424/68; 514/770; 514/873; 514/947; 514/948; 514/969
[58] Field of Search ....................... 424/46, 47, 68, 66; 514/873, 969, 770, 947, 948

[56] References Cited

U.S. PATENT DOCUMENTS

| | | | |
|---|---|---|---|
| 3,773,683 | 11/1973 | Aubert | 424/46 |
| 3,968,203 | 7/1976 | Spitzer et al. | 424/47 |
| 4,152,416 | 5/1979 | Spitzer et al. | 424/47 |
| 4,450,151 | 5/1984 | Shinozaua | 424/46 |
| 4,605,554 | 8/1986 | Prussin et al. | 424/66 |

FOREIGN PATENT DOCUMENTS

2018590 10/1979 United Kingdom ................. 424/47

Primary Examiner—Dale R. Ore
Attorney, Agent, or Firm—Oblon, Spivak, McClelland, Maier & Neustadt

[57] ABSTRACT

A novel composition for antiperspirant aerosol comprises an antiperspirant substance, a silicone-treated clay mineral and an oil substance.

When the composition is sprayed over the skin, sweat can readily evaporate immediately after spraying and even after perspiration. Thus, the composition ensures a very good feel in use.

17 Claims, 2 Drawing Sheets a : Inventive Composition 11
b : Comparative Composition 12

FIG. I a : Inventive Composition 11 b : Comparative Composition 12

COMPOSITION FOR ANTIPERSPIRANT AEROSOL

This application is a continuation of application Ser. No. 06/943,704, filed on Dec. 19, 1986, now abandoned.

BACKGROUND OF THE INVENTION (1) Field of the Invention

This invention relates to compositions for antiperspirant aerosols and more particularly, to compositions for antiperspirant aerosols which are very agreeable in use.

(2) Description of the Prior Art

Heretofore, a variety of antiperspirants have been used to suppress perspiration and prevent offensive odors such as an axillary odor caused by decomposition of sweat. The most popular antiperspirants are compositions for antiperspirant aerosol which comprise antiperspirant substances consisting of metal salts such as aluminum salts, clay minerals such as talc which serve to impart a slippery feeling to the skin, and oil components for permitting the antiperspirant substances to be deposited on the skin.

In recent years, many attempts have been made to suppress wetness immediately after spraying and after sweating and to give an agreeable feel in use. Examples of such attempts include formulating into the composition clay minerals such as talc having a plate crystal structure, micronized talc, or spherical particles (Japanese Patent Application Laid-open No. 52-99236), or adding a volatile silicone to the oil component (Japanese Patent Application Laid-open No. 56-29912).

However, these attempts have the following various problems. When plate crystal talc or its micronized product is added, the wetness immediately after spraying can be suppressed to a certain extent but a satisfactory effect of suppressing wetness with perspiration cannot be obtained. With spherical particles, wetness can be suppressed to a certain extent upon spraying, even though only small amount of the particles are added to the formulation. However, such formulation is not yet effective for supressing wetness with sweat. If a greater amount of the spherical particles is formulated, whiteness after spraying increases with a problem of appearance. In case of an aerosol composition using a volatile silicone in an oil component, any significant effect cannot be obtained when a small amount of the volatile silicone is used. On the other hand, when a greater amount is used, several problems arise: it undesirably takes a long time before volatilization; a spray pattern takes a ring form; the feel in use immediately after spraying is objectionable; and adherence of the powder lowers. Accordingly, there is a strong demand for development of a composition for antiperspirant aerosol which is not felt wet not only immediately after spraying, but also after sweating and which permits sweat to be readily volatalized with a good feel in use.

SUMMARY OF THE INVENTION

The present inventors made intensive studies to solve the above problems and, as a result, found that a composition for antiperspirant aerosol comprising a silicone-treated clay mineral was free of wetness not only immediately after spraying, but also after perspiration. The present invention was accomplished based on the above finding.

More particularly, the present invention provides a composition for antiperspirant aerosol comprising an antiperspirant substance, a siliconetreated clay mineral and an oil substance.

DESCRIPTION OF THE INVENTION AND PREFERRED EMBODIMENTS

Figure 1:
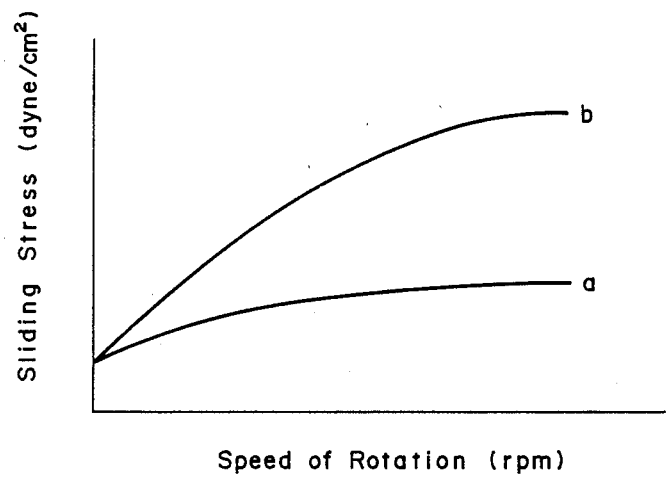
FIG. 1 is a graphical representation of the relation between rotation speed and sliding stress after addition of water to a composition of the invention and a comparative composition.

The clay minerals used in the present invention should be treated with silicones. The clay minerals may be any known powders ordinarily used in cosmetics and are not thus critical. Examples of the minerals include inorganic powders such as talc, sericite, mica, silica, kaolin and the like. Of these, sericite, or talc having an average particle size of 1 to 20 micrometers and a plate crystal structure is preferred. The silicones used to treat these clay minerals, i.e. organopolysiloxanes, are not critical so far as they are liquid at normal temperatures. Preferable examples include dimethyl polysiloxane, methylphenyl polysiloxane, methylhydrogen polysiloxane and the like.

The treatment of clay minerals with silicones is preferably effected using 1.0 to 5.0 wt% of a silicone on the basis of clay mineral. For instance, 10 to 20 wt% of a 10% silicone solution in methylene chloride is sprayed over the mineral and baked at 100° C. for 2 hours.

The oil components may be any oils used in ordinary cosmetics and include, for example, liquid paraffin, isopropyl myristate, isopropyl palmitate, squalane, 2-octyldodecyl myristate, neopentylglycol-2-ethyl hexanoate, 2-octyldodecyl oleate, myristyl myristate, and volatile cyclic silicones. These may be used singly or in combination. Of these, combinations of isopropyl myristate, isopropyl palmitate and the like with cyclic silicones are preferred. The cyclic silicones are preferably those which have 4 or 5 dimethyl siloxane units or mixtures thereof.

The antiperspirant substances may be any substances which have been accepted as having the antiperspirant action. Examples of these substances include aluminum or zirconium astringent salts such as aluminum halides, aluminum hydroxyhalides, zirconyl oxyhalides, zirconyl hydroxyhalides and the like, or astringent complexes of these salts, which may be used singly or in combination. Of these, aluminum astringent salts are preferred. Typical salts include aluminum chloride and aluminum hydroxyhalides of the general formula, $Al_2(OH)_l X_m \cdot nH_2O$ in which X represents a chlorine atom, a bromine atom or an iodine atom, $l$ and $m$ are, respectively, an integer of from 2 to 5 provided that $l+m$ is 6, and n is an integer of from 1 to 6. Among them, aluminum hydroxychloride of the formula, $Al_2(OH)_l Cl_m \cdot nH_2O$, is preferred.

The composition of the invention has a formulation comprising 10 to 80 wt% (hereinafter referred to simply as %), preferably from 20 to 50%, of a silicone-treated clay mineral, from 10 to 60%, preferably from 30 to 50%, of an oil component. If a preferable combination of isopropyl myristate and a cyclic silicone is used as the oil component, the cyclic silicone is favorably used in an amount of from 30 to 50%, preferably from 40 to 50%, of isopropyl myristate. When the cyclic silicone is used in excess, the antiperspirant substance and the powder of clay mineral are unlikely to deposit. In applications, such a composition gives a kind of "squeezing" feel after use. On the contrary, less amounts unfavorably increase oiliness of isopropyl myristate.

The composition of the invention may further comprise bactericides, perfumes and the like which are ordinary in known compositions for antiperspirant aerosol.

When the composition of the invention is used as an antiperspirant of the aerosol type, a suitable propellant is added to the composition and filled in a sealed container having an aerosol valve.

The propellants are not critical so far as they are liquefied products which are gaseous at normal temperatures and pressures and are immiscible with solid components of the composition. Examples of the propellants include hydrocarbons such as propane, butane and the like, halogenated hydrocarbons such as dichlorofluoromethane, 1,2-dichloro-1,1,2,2-tetrafluoroethane, trichloromonofluoromethane and the like, and mixtures thereof.

The amount of the propellant to be added is preferably such that the amount of the composition of this invention may be in the range of from 2 of 55% of the total composition comprising the propellant. The antiperspirant substance and the clay mineral of the total composition after addition of the propellant are used in amounts ranging from 1 to 10%, preferably from 2 to 5%. Too large amounts are unfavorable because the spray will diffuse over a wide area or the aerosol valve may clog. Less amounts do not produce a satisfactory effect of the invention.

The composition for antiperspirant aerosol of the invention is formulated with a silicone-treated clay mineral. Since the silicone-treated clay mineral is significantly hydrophobic on the surface thereof, the mineral which has been deposited on the surface of the skin has a low physical viscoelasticity even after perspiration and does not absorb sweat, thus promoting the sweat to evaporate.

As described above, when the composition of the invention is sprayed over the skin, sweat can readily evaporate immediately after spraying and even after perspiration. Thus, the composition ensures a very good feel in use since it involves little wetness.

The present invention is described by way of examples, which should not be construed as limiting the present invention.

EXAMPLE 1

Compositions for antiperspirant aerosol of the formulations shown in Table 1 were prepared and the respective compositions were mixed with propellants shown in Table 2 to obtain antiperspirants of the aerosol type (lower portion of Table 2). Ten expert panelists organoleptically evaluated the antiperspirants with respect to the feel in use immediately after spraying and also after perspiration.

(Preparation)

Oil components were uniformly dissolved at room temperature, with which the respective powder phases were uniformly mixed, followed by packaging along with a propellant according to a standard aerosol packaging method.

(Evaluation Standards of Feel in Use)

The antiperspirants of the invention and for comparison shown in Tables 1 and 2 were, respectively, evaluated and the test items were each expressed as an average value of the organoleptic evaluation according to the following standards.

5: very excellent
4: excellent
3: moderate
2: poor
1: very poor

The results are shown in Table 3.

TABLE 1

| Ingredients | Inventive Composition | | | | Comparative Composition | | | | | |
|---|---|---|---|---|---|---|---|---|---|---|
| | 1 | 2 | 3 | 4 | 5 | 6 | 7 | 8 | 9 | 10 |
| Oil Phases | | | | | | | | | | |
| Isopropyl myristate | 16.0 | 20.0 | 20.0 | 16.0 | 32.0 | 32.0 | 32.0 | 16.0 | 10.0 | — |
| Cyclic dimethyl siloxane (made by Nippon Unicar; VS-7349, n=4/5=85/15) | 16.0 | 20.0 | 20.0 | 16.0 | — | — | — | 16.0 | 22.0 | 55.0 |
| Trichlosan (bactericide) | 0.2 | 0.2 | 0.2 | 0.2 | 0.2 | 0.2 | 0.2 | 0.2 | 0.2 | 0.2 |
| Perfume | 3.80 | 3.80 | 3.80 | 3.80 | 3.80 | 3.80 | 3.80 | 3.80 | 3.80 | 3.80 |
| Powder Phases | | | | | | | | | | |
| Aluminum hydroxychloride (anhidrotic substance; Rokuron P) | 32.0 | 28.0 | 6.0 | 32.0 | 32.0 | 32.0 | 32.0 | 32.0 | 32.0 | 23.40 |
| Talc | — | — | — | — | 32.0 | — | — | 32.0 | 32.0 | 17.60 |
| Micronized talc (made by Asada Seifun K.K., JET-S MMR) | — | — | — | — | — | 32.0 | — | — | — | — |
| Spherical talc (made by Iwase Shoten K.K., Microsphere M) | — | — | — | — | — | — | 32.0 | — | — | — |
| Silicone-treated talc (Miyoshi Kasei K.K., JA-46R) | 32.0 | 28.0 | 50.0 | — | — | — | — | — | — | — |
| Silicone-treated sericite (Toshoku Pigment Co., Ltd., JS-610) | — | — | — | 32.0 | — | — | — | — | — | — |
| Total (%) | 100.0 | 100.0 | 100.0 | 100.0 | 100.0 | 100.0 | 100.0 | 100.0 | 100.0 | 100.0 |

TABLE 2

| Ingredients | Inventive Composition | | | | Comparative Product | | | | | |
|---|---|---|---|---|---|---|---|---|---|---|
| | 1 | 2 | 3 | 4 | 5 | 6 | 7 | 8 | 9 | 10 |
| Propellants | | | | | | | | | | |

TABLE 2-continued

| Ingredients | Composition (%) | | | | | | | | | |
|---|---|---|---|---|---|---|---|---|---|---|
| | Inventive Composition | | | | Comparative Product | | | | | |
| | 1 | 2 | 3 | 4 | 5 | 6 | 7 | 8 | 9 | 10 |
| Flon-11 (dichlorodifluoromethane) | 52.60 | ← | ← | ← | ← | ← | ← | ← | ← | ← |
| Flon-12 (trichloromonofluoromethane) | 22.10 | ← | ← | ← | ← | ← | ← | ← | ← | ← |
| LPG (2.7 kg/Cm²G) (liquefied petroleum gas) | 25.30 | ← | ← | ← | ← | ← | ← | ← | ← | ← |
| Total (%) | 100.0 | ← | ← | ← | ← | ← | ← | ← | ← | ← |
| Final Antiperspirant Composition | | | | | | | | | | |
| Mixed powder phase | 3.20 | 2.80 | 2.80 | 3.20 | 3.20 | 3.20 | 3.20 | 3.20 | 3.20 | 2.05 |
| Mixed oil phase | 1.80 | 2.20 | 2.20 | 1.80 | 1.80 | 1.80 | 1.80 | 1.80 | 1.80 | 2.9 |
| Propellant | 95.0 | 95.0 | 95.0 | 95.0 | 95.0 | 95.0 | 95.0 | 95.0 | 95.0 | 95.0 |
| Total (%) | 100.0 | 100.0 | 100.0 | 100.0 | 100.0 | 100.0 | 100.0 | 100.0 | 100.0 | 100.0 |

TABLE 3

| Evaluation Item | Results of Evaluation | | | | | | | | | |
|---|---|---|---|---|---|---|---|---|---|---|
| | Inventive Composition | | | | Comparative Composition | | | | | |
| | 1 | 2 | 3 | 4 | 5 | 6 | 7 | 8 | 9 | 10 |
| Prior to Perspiration | | | | | | | | | | |
| dryness | 4.7 | 4.5 | 4.8 | 4.3 | 4.0 | 3.7 | 3.5 | 4.0 | 3.8 | 3.3 |
| smoothness | 4.8 | 4.5 | 4.9 | 4.5 | 4.3 | 4.0 | 3.9 | 3.8 | 3.7 | 3.5 |
| wetness | 4.8 | 4.5 | 4.7 | 4.8 | 4.3 | 4.5 | 4.5 | 4.3 | 3.8 | 4.0 |
| After Perspiration | | | | | | | | | | |
| dryness | 4.2 | 4.3 | 4.5 | 4.6 | 2.9 | 2.6 | 3.5 | 2.7 | 2.8 | 3.5 |
| smoothness | 4.5 | 4.7 | 4.3 | 4.5 | 2.8 | 2.7 | 3.9 | 2.8 | 2.6 | 3.9 |
| wetness | 4.9 | 4.7 | 4.8 | 4.5 | 2.3 | 2.2 | 3.5 | 2.2 | 2.0 | 2.8 |

As will be apparent from the above, the antiperspirants comprising a composition of the invention have especially good feels in use after perspiration.

EXAMPLE 2

Compositions for antiperspirant aerosol of the formulations of oil and powder phases shown in Table 4 were prepared, to which propellants indicated in Table 4 were added to give antiperspirant aerosol of the formulations shown at a lower portion of Table 4. These antiperspirants were subjected to measurement of a sliding stress as an index of wetness after perspiration. The results are shown in FIG. 1, which reveals that the antiperspirant of the invention has a lower sliding stress than the comparative antiperspirant and thus, has a low physical viscoelasticity after perspiration, with less degrees of roughness and wetness.

(Measuring Method)

The antiperspirants of the invention and for comparison were each sprayed in a given amount over a sample base with a predetermined area under conditions of 30° C. Thereafter, a given amount of water instead of sweat was dropped and a sliding stress was measured by means of a rotational viscometer.

The ratio of water versus powder was powder : water=2.5:0.35. The measurement was made at 30° C. using Rotovisco (made by Haarque Co., Ltd.).

TABLE 4

| Ingredients | Composition (%) | |
|---|---|---|
| | Inventive Composition 11 | Comparative Composition 12 |
| Oil Phase | | |

TABLE 4-continued

| Ingredients | Composition (%) | |
|---|---|---|
| | Inventive Composition 11 | Comparative Composition 12 |
| 2-octyldodecyl myristate | 25.0 | 25.0 |
| decamethyl cyclopentasiloxane (made by Nippon Unicar Co., Ltd., VS-7158) | 25.0 | 25.0 |
| trichlosan | 0.20 | 0.20 |
| perfume | 3.80 | 3.80 |
| Powder Phase | | |
| aluminium hydroxychloride | 23.0 | 23.0 |
| talc | 23.0 | — |
| silicone-treated talc | — | 23.0 |
| Total (%) | 100.0 | 100.0 |
| Propellant | | |
| Flon-11 | 52.60 | 52.60 |
| Flon-12 | 22.10 | 22.10 |
| LPG(2.7 kg/cm²G) | 25.30 | 25.30 |
| Total (%) | 100.0 | 100.0 |
| Antiperspirant Composition | | |
| mixed powder phase | 3.22 | 3.22 |
| mixed oil phase | 3.78 | 3.78 |
| propellant | 93.0 | 93.0 |
| Total (%) | 100.0 | 100.0 |

EXAMPLE 3

The silicone-treated talc and non-treated talc formulated in the compositions of the invention, to which water was added, were, respectively, evaluated with respect to dissipation of sweat.

(Measuring Test)

Figure 2:
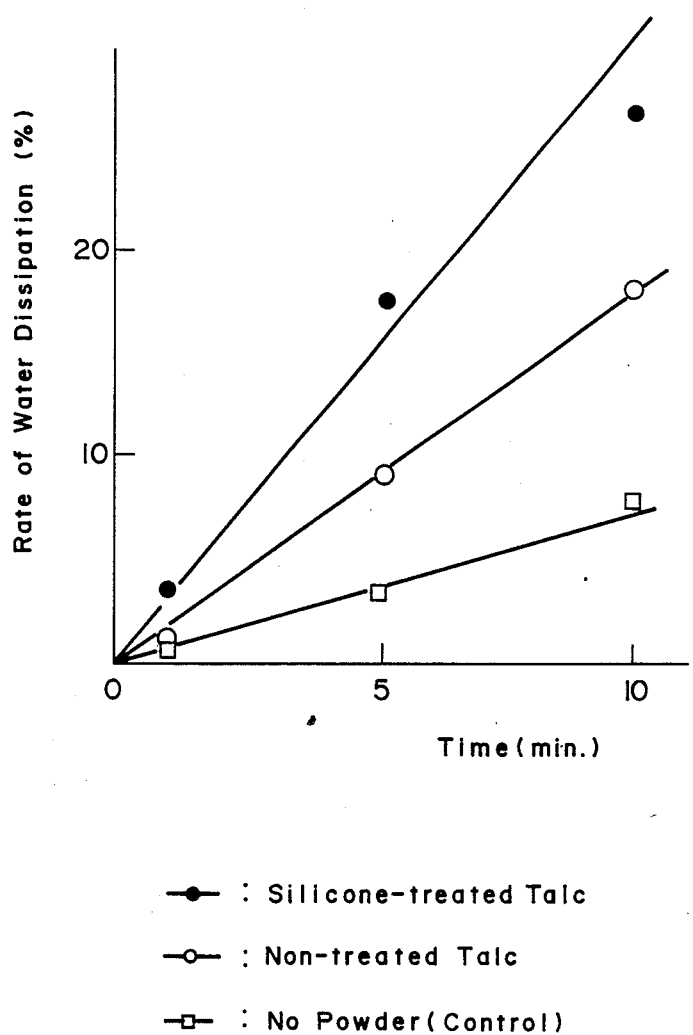
FIG. 2 is a graphical representation of the relation between time and rate of dissipation of moisture where water-added silicone-treated talc and non-treated talc are allowed to stand.

Silicone-treated talc (made by Miyoshi Kasei Co., Ltd., JA-46R) and non-treated talc were each weighed in a constant amount and placed in a dish, to which the same amount of water was added, followed by allowing it to stand at 30° C. and 50% R.H. The variation of the weight was measured with time. The loss in weight was determined as a rate of moisture dissipation. The results are shown in FIG. 2. From the results, it will be seen that the silicone-treated talc has the function of promoting the dissipation of moisture, i.e. sweat.

What is claimed is:

1. In an antiperspirant aerosol composition, comprising:
    an aluminum or a zirconium astringent salt;
    an oil which is at least one member selected from the group consisting of liquid paraffin, isopropyl myristate, isopropyl palmitate, squalane, 2-octyldodecyl oleate, myristyl myristate, and volatile cyclic silicones; and a propellent, wherein the improvement comprises preventing wetness immediately after spraying by incorporating;

a liquid organopolysiloxane-treated talc or sericite;

wherein the amount of said astringent salt and said liquid organopolysiloxane treated talc or sericite is 1 to 10 wt.% of said antiperspirant aerosol composition, and wherein the total amount of said astringent salt, said oil, and said liquid organopolysiloxane treated talc or sericite is 2 to 55 wt.% of said antiperspirant aerosol composition comprising the propellant.

2. The composition of claim 1, wherein said sericite or talc has an average particle size of 1 to 20 micrometers and a plate crystal structure.

3. The composition of claim 1, wherein said organopolysiloxane is dimethylpolysiloxane methylphenylpolysiloxane, or methylhydrogenpolysiloxane.

4. The composition of claim 1, wherein said oil substance is isopropyl myristate, isopropyl palmitate or a cyclic silicone.

5. The composition of claim 4, wherein said cyclic silicone is a silicone having four or five dimethylsiloxane units.

6. The composition of claim 1, wherein said aluminum astringent salt is an aluminum halide or an aluminum hydroxyhalide.

7. The composition of claim 1, wherein said zirconium astringent salt is a zirconyl oxyhalide or a zirconyl hydroxyhalide.

8. The composition of claim 1, comprising an aluminum astringent salt.

9. The composition of claim 1, comprising zirconium astringent salt.

10. The composition of claim 1, wherein said aluminum astringent salt is aluminum chloride or an aluminum hydroxyhalide of the formula $Al_2(OH)_lX_m \cdot nH_2O$, wherein X is a chlorine atom, a bromine atom or an iodine atom, l and m are, respectively, an integer of from 2 to 5 provided that $l+m$ is 6, and n is an integer of from 1 to 6.

11. The composition of claim 10, wherein said aluminum astringent salt is an aluminum hydroxychloride of the formula $Al_2(OH)_lCl_m \cdot nH_2O$.

12. The composition of claim 1, comprising a bacteriocide or a perfume.

13. The composition of claim 1, wherein said propellant comprises a hydrocarbon or a halogenated hydrocarbon.

14. The composition of claim 1, wherein said propellant is propane, butane, dichlorofluoromethane, 1,2-dichloro-1,1,2,2-tetrafluoroethane or trichloromonofluoromethane.

15. The composition of claim 1, wherein said talc or sericite is treated with from 1.0 to 5.0 wt% of said organopolysiloxane on the basis of said talc or said sericite.

16. The composition of claim 1, comprising a liquid organopolysiloxane-treated talc.

17. The composition of claim 1, comprising a liquid organopolysiloxane-treated sericite.

* * * * *